United States Patent
Stevenson et al.

(10) Patent No.: US 10,188,861 B2
(45) Date of Patent: Jan. 29, 2019

(54) BIOABSORBABLE OR PARTIALLY-BIOABSORBABLE BONE GROWTH STIMULATOR SYSTEM AND METHOD FOR MANUFACTURING A BIOABSORBABLE OR PARTIALLY-BIOABSORBABLE BONE-REGENERATION STIMULATOR SYSTEM

(71) Applicant: Warsaw Orthopedic, Inc, Warsaw, IN (US)

(72) Inventors: Tyler S. Stevenson, Tempe, AZ (US); Richard L. Brown, Mesa, AZ (US); Todd A. Kallmyer, Tempe, AZ (US); Matthew M. Morrison, Cordova, TN (US); Sneha Saikia, Tempe, AZ (US); Randal Schulhauser, Phoenix, AZ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 135 days.

(21) Appl. No.: 15/084,189

(22) Filed: Mar. 29, 2016

(65) Prior Publication Data
US 2017/0281943 A1    Oct. 5, 2017

(51) Int. Cl.
*A61N 1/36* (2006.01)
*A61N 1/378* (2006.01)

(52) U.S. Cl.
CPC ....... *A61N 1/36035* (2013.01); *A61N 1/3787* (2013.01)

(58) Field of Classification Search
None
See application file for complete search history.

(56) References Cited

U.S. PATENT DOCUMENTS

| | | | |
|---|---|---|---|
| 5,447,533 | A | 9/1995 | Vachon et al. |
| 6,605,089 | B1 | 8/2003 | Michelson |
| 8,968,926 | B2 | 3/2015 | Hodgkinson et al. |
| 8,968,927 | B2 | 3/2015 | Hodgkinson et al. |
| 2003/0171793 | A1 | 9/2003 | Carter et al. |
| 2005/0187591 | A1* | 8/2005 | Carter .............. A61N 1/32 607/46 |
| 2010/0160999 | A1* | 6/2010 | Epstein ............. C12M 35/02 607/50 |
| 2010/0211172 | A1 | 8/2010 | Bellamkonda et al. |
| 2012/0203307 | A1 | 8/2012 | Schroeppel et al. |

(Continued)

OTHER PUBLICATIONS

International Search Report and Written Opinion for PCT/US2017/024537 the counterpart application dated Jun. 9, 2017, 11 pages.

*Primary Examiner* — Ankit D Tejani (57) ABSTRACT

A bone growth simulator system. A bioabsorbable electric circuit is encapsulated in a modified alginate known-time dissolving capsule having a rate of dissolving proportional to the thickness of the capsule. The electronic circuit is powered by a power source. The power source can be inside the capsule or outside the capsule, and can be bioabsorbable or at least biocompatible. An operational amplifier maintains constant current through the circuit. The current stimulates bone growth in bones adjacent to the circuit. The capsule and electric circuit dissolve after completion of the therapy.

20 Claims, 8 Drawing Sheets

(56) References Cited

U.S. PATENT DOCUMENTS

2015/0088222 A1* 3/2015 Bettinger ............... A61N 1/375
  607/40
2015/0230729 A1* 8/2015 Zdeblick ................ A61B 5/073
  600/302

* cited by examiner

BIOABSORBABLE OR PARTIALLY-BIOABSORBABLE BONE GROWTH STIMULATOR SYSTEM AND METHOD FOR MANUFACTURING A BIOABSORBABLE OR PARTIALLY-BIOABSORBABLE BONE-REGENERATION STIMULATOR SYSTEM

FIELD OF THE INVENTION

The present invention relates to a bioabsorbable, or partially-bioabsorbable, bone growth simulator system for use in the field of bone regeneration therapy, and more particularly for use in the field of spinal bone regeneration therapy; and a method for manufacturing the same.

DESCRIPTION OF THE PRIOR ART

Figure 6:
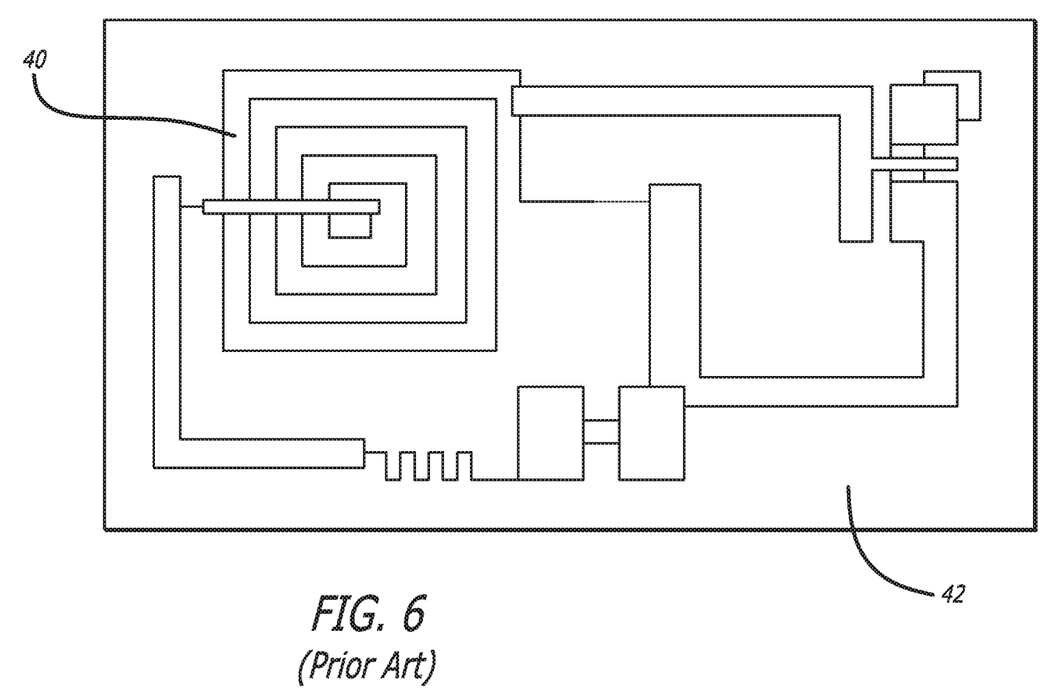
FIG. 6 is a schematic view of a prior art biocompatible circuit on a bioabsorbable substrate.
Figure 7:
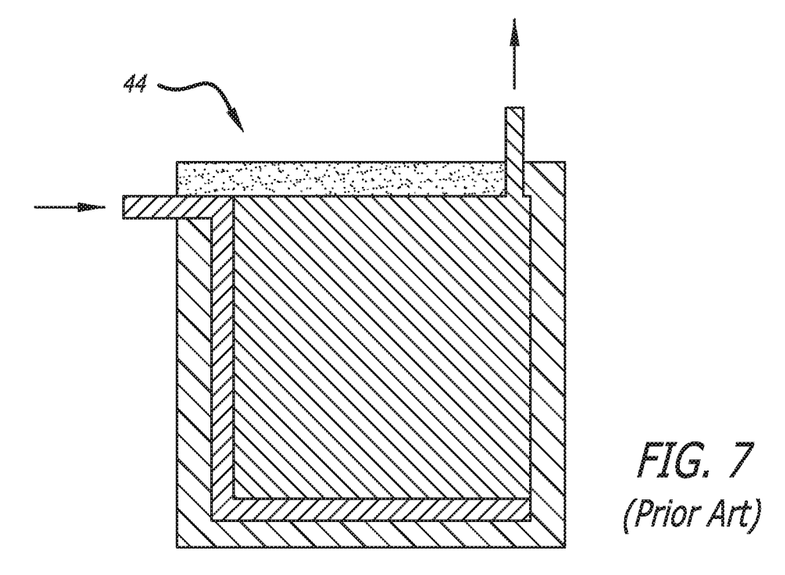
FIG. 7 is a cross-sectional view of a prior art bioabsorbable battery.

Electrical bone growth stimulator systems are known. The use of related art bone growth stimulator systems, particularly spinal bone growth stimulator systems for treatment of various spinal pathologies and disorders, however, is limited by such restrictions as patient compliance issues, cost/reimbursement issues, device size and complexity, and implant procedure complexity. Known bone growth stimulator systems have a useful life typically lasting less than six months before they need to be removed. Three to six months also is the typical time needed for completion of the bone regeneration therapy. Since surgery to remove the device is uncomfortable and expensive, it is desirable to have a bioabsorbable bone growth stimulator system that is consumed, or at least partially consumed, by the patient's body. Bioabsorbable electronics are under development, which include discrete electrical components 40 rendered in biocompatible materials on bioabsorbable insulated substrates 42 made of, e.g., silk. These substrates 42, however, have unpredictable dissolution rates, making these bioabsorbable electronics insufficiently reliable for use in bone regeneration therapy, particularly spinal bone regeneration therapy. Bioabsorbable batteries 44 also are known, but known bioabsorbable batteries have large "footprints," which make them incompatible with the bodies of many patients.

SUMMARY OF THE INVENTION

It is an object of the present invention to provide a bioabsorbable or partially-bioabsorbable bone growth stimulator system which obviates one or more of the shortcomings in the related art.

It is another object of the present invention to provide a bone growth stimulator system for use in bone regeneration therapy. In one embodiment, the system includes a bioabsorbable electric circuit, which includes at least one operational amplifier. In one embodiment, a bioabsorbable capsule encloses the electric circuit. In one embodiment, the capsule has a selected capsule thickness and a known dissolution time. In one embodiment, the known dissolution time is directly related to the capsule thickness. In one embodiment, the capsule thickness is selected so that the capsule, and the electric circuit, will be bioabsorbed after completion of the bone regeneration therapy.

In one embodiment, the power source includes a battery, providing a voltage to the circuit, thereby defining a current therethrough.

In one embodiment, as a result of the at least one operational amplifier in the electric circuit, the voltage and current remain substantially constant.

In one embodiment, the battery is located inside the capsule, and is directly coupled to the electric circuit.

In one embodiment, the battery is located outside the capsule.

In one embodiment, the battery located outside the capsule is inductively coupled to the electric circuit.

In one embodiment, the battery located outside the capsule is capacitively coupled to the electric circuit.

In one embodiment, the battery is bioabsorbable.

In one embodiment, the battery is at least biocompatible.

It is a further object of the present invention to provide a method of manufacturing a bone growth stimulator system for use in bone regeneration therapy.

In one embodiment, the method includes applying at least a polyimide layer on a substrate.

In one embodiment, the method further includes applying a photoresist layer on the at least one polyimide layer.

In one embodiment, the method further includes applying a photomask above the photoresist layer, the photomask including an outline of an electric circuit. The outline of the electric circuit includes outlines of discrete electrical components, including at least an outline of at least one operational amplifier.

In one embodiment, the method further includes exposing the photoresist layer to light, defining at least one layer of a Mg or MgO electric circuit on the substrate. The at least one layer of the electric circuit is bioabsorbable, and includes at least one operational amplifier.

In one embodiment, the method further includes processing the at least one polyimide layer and the photoresist layer. The processing removes the at least one polyimide layer and the photoresist layer from the substrate.

In one embodiment, the method further includes enclosing the electric circuit in a bioabsorbable capsule having a selected capsule thickness and a known dissolution time.

In one embodiment, the capsule is made of water-soluble modified alginate.

In one embodiment, the known dissolution time is directly related to the selected capsule thickness.

In one embodiment, the capsule thickness is selected to bring about dissolution of the bioabsorbable capsule and the bioabsorbable electric circuit following completion of the bone growth therapy.

In one embodiment, the method further includes coupling a power source to the electric circuit. The power source provides an electric voltage to, and defines an electric current through the electric circuit.

In one embodiment, the at least one operational amplifier maintains a constant voltage and current in the electric circuit.

In one embodiment, coupling the power source to the electric circuit includes coupling the electric circuit to a power source which is defined external to the capsule.

In one embodiment, the power source is bioabsorbable, and the bone growth stimulator system is bioabsorbable.

In one embodiment, the power source is at least biocompatible, and the bone growth stimulator system is at least partially bioabsorbable.

It is a further object of the invention to implant the bone growth stimulator system adjacent one or more bones experiencing various disorders or pathologies to provide bone regeneration therapy.

In one embodiment, the one or more bones include spinal bones, including, but not limited to, adjacent vertebral bodies.

In one embodiment, current through the electric circuit generates bone growth in the one or more bones.

In one embodiment, bioabsorption of the bioabsorbable components of the system occurs following completion of the bone regeneration therapy.

These and other objects of the present invention will be apparent from review of the following specification and the accompanying drawings.

DETAILED DESCRIPTION OF THE PREFERRED EMBODIMENT

In accordance with the invention, a bioabsorbable or partially-bioabsorbable bone growth stimulator system 10 is provided for use in bone regeneration therapy, for example, but not by way of limitation, bone growth between two adjacent vertebral bodies.

In one embodiment, as embodied in FIGS. 1A-1C and 3, the system includes a bioabsorbable electric circuit 12. In one embodiment, the electric circuit 12 is made of Mg or MgO.

In one embodiment, as embodied in FIGS. 1A-1C and 3, the electric circuit 12 includes an operational amplifier 14, a plurality of resistors 15, at least one transistor 17, two ammeters AM1 and AM2, and two voltmeters VM1 and VM2.

In one embodiment, as depicted in FIGS. 1A-1C, 3, and 5, a bioabsorbable capsule 16 encloses the bioabsorbable electric circuit 12. The bioabsorbable capsule 16 has a thickness with a known dissolution time. The known dissolution time is directly proportional to the thickness of the capsule 16. The invention is not limited to a specific thickness of the capsule 16. The thickness is selected in order to result in bioabsorption of at least the capsule 16 and the electric circuit 12 after completion of the bone regeneration therapy. In one embodiment, the bioabsorbable capsule is made of water soluble modified alginate.

In one embodiment, a power source is configured to be electrically coupled to the electric circuit 12.

In one embodiment, the power source is a battery 18, applying a voltage to the electric circuit 12, as measured by the voltmeters VM1 and VM2. The voltage applied across the resistors 15 defines a current through the electric circuit 12, as measured by the ammeters AM1 and AM2.

Figure 1A:
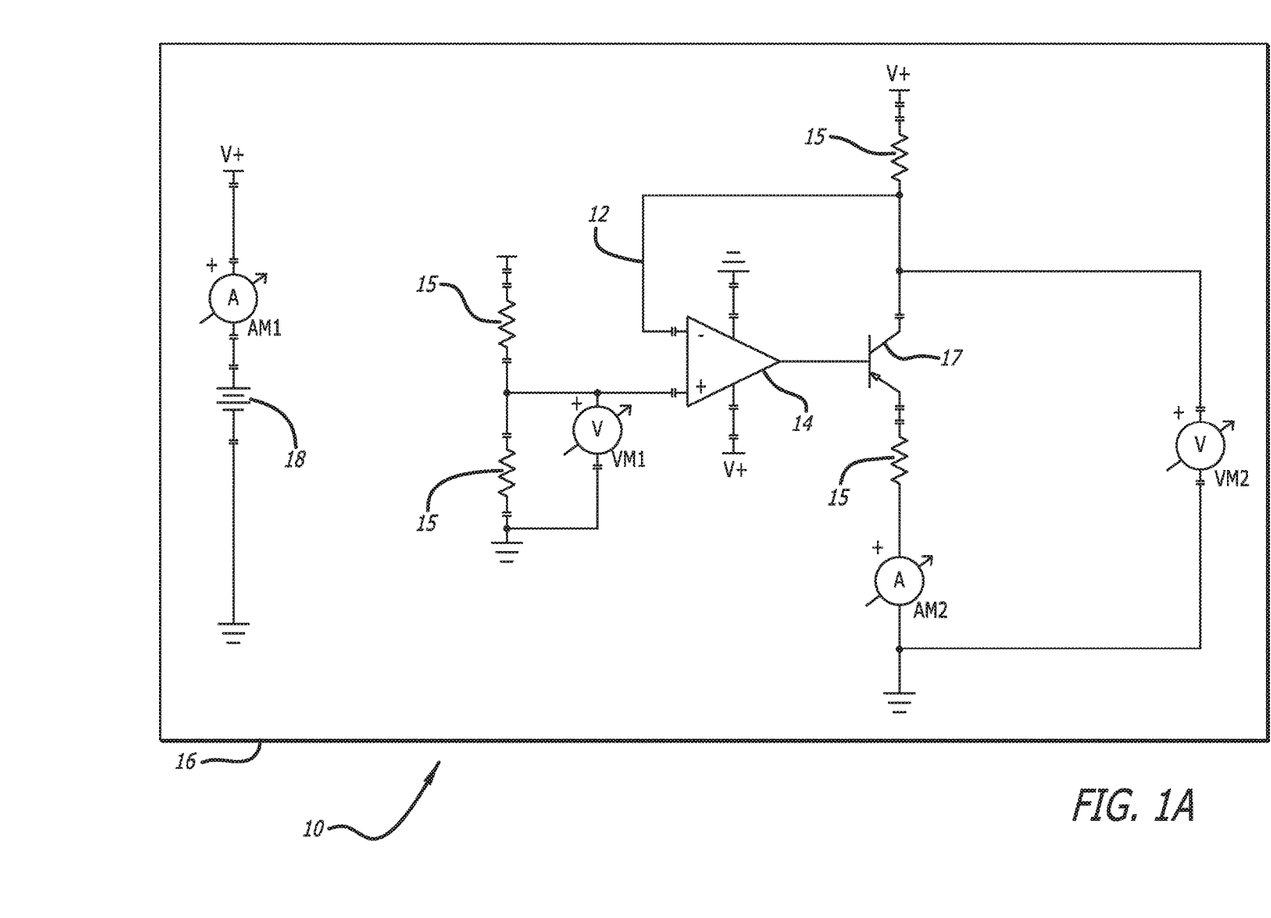
FIG. 1A is a schematic diagram of one embodiment of a bioabsorbable bone growth stimulator system in accordance with the present invention.
Figure 3:
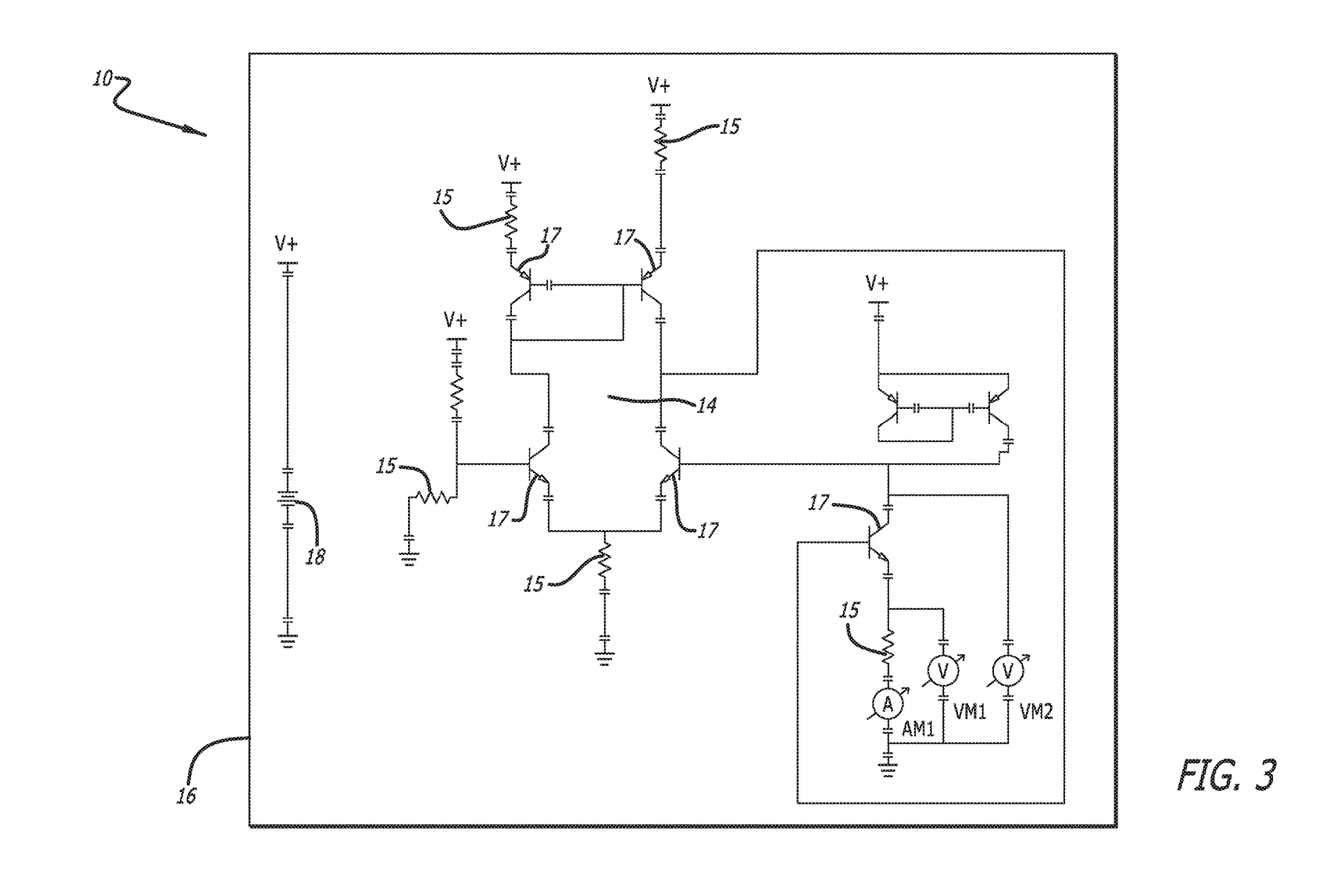
FIG. 3 is a schematic diagram of one embodiment of a bioabsorbable bone growth stimulator system in accordance with the present invention.

In one embodiment, as depicted in FIGS. 1A and 3, the battery 18 can be provided inside the capsule 16.

Figure 1B:
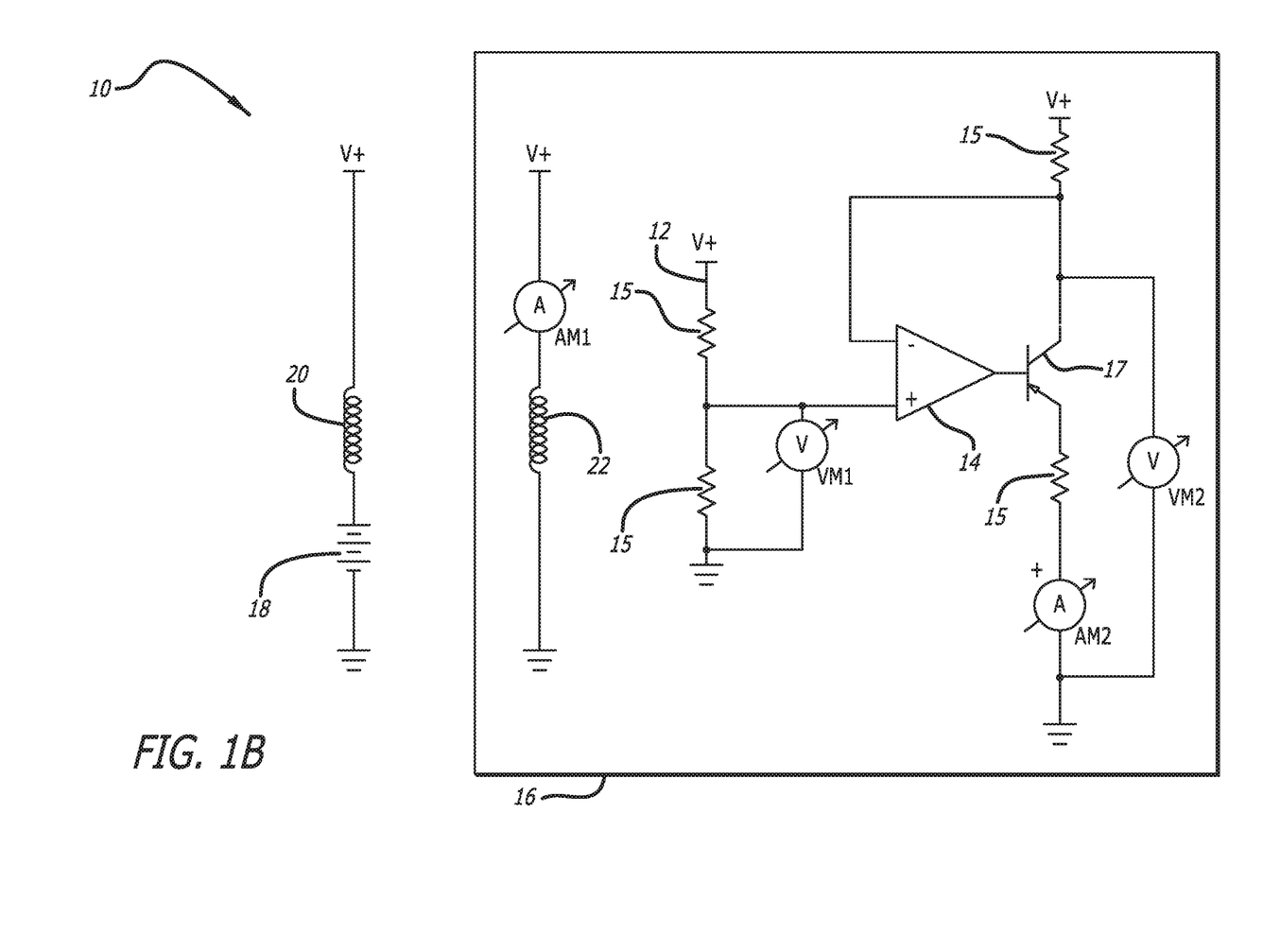
FIG. 1B is a schematic diagram of one embodiment of at least a partially-bioabsorbable bone growth stimulator system in accordance with the present invention.
Figure 1C:
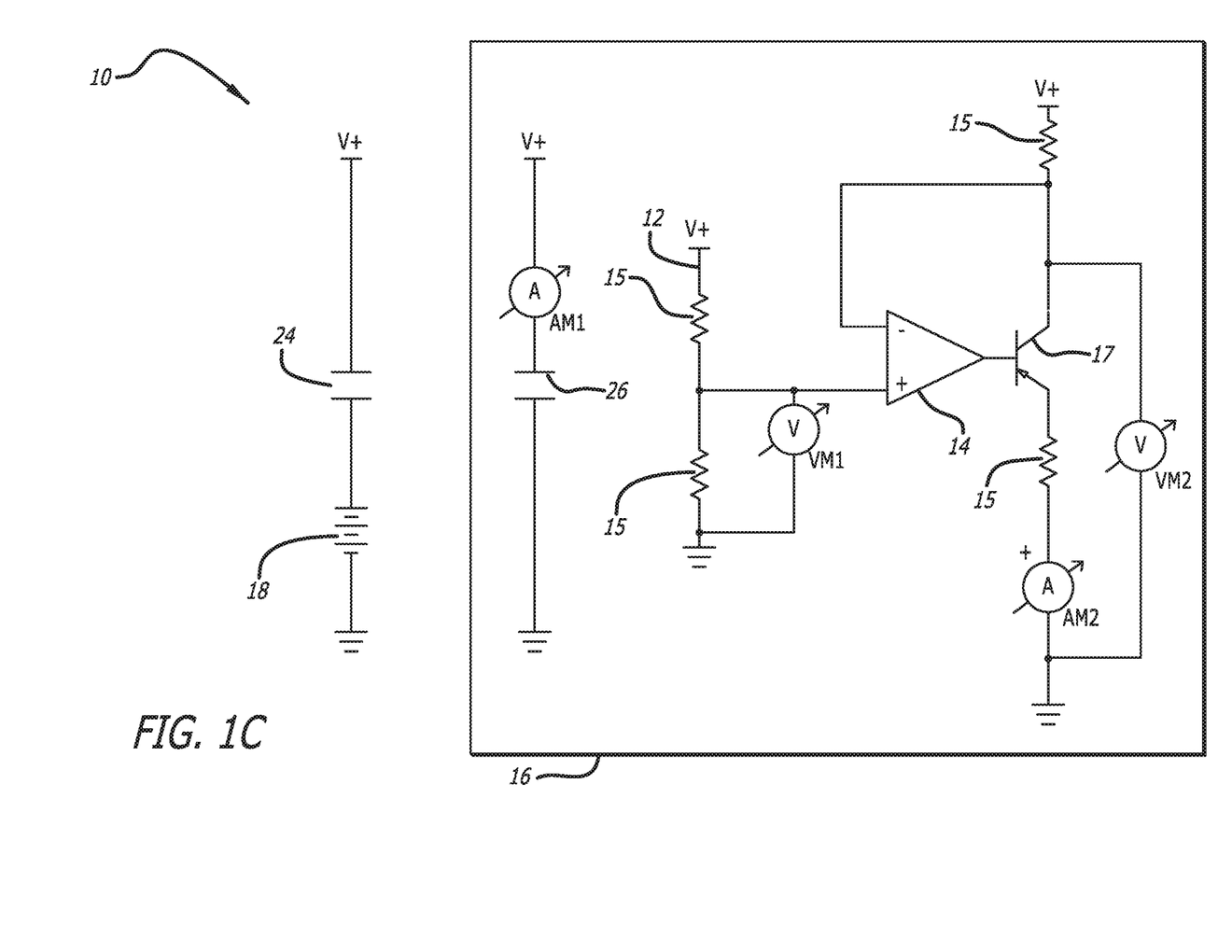
FIG. 1C is s a schematic diagram of one embodiment of at least a partially-bioabsorbable bone growth stimulator system in accordance with the present invention.

In one embodiment, as depicted in FIGS. 1B and 1C, the battery 18 can be provided outside the capsule 16. In one embodiment, the battery 18 provided outside the capsule 16 is configured to have a relatively small "footprint" in a human body.

In one embodiment, as depicted in FIG. 1A, the battery 18, provided inside the capsule 16, is directly coupled to the electric circuit 12.

In one embodiment, as depicted in FIG. 1B, the power source includes a battery 18, and a pair of coils 20 and 22. The battery 18 and the first coil 20 are provided outside the capsule 16. A second coil 22 is provided inside the capsule 16. The two coils 20 and 22 are inductively coupled together to supply power to the electric circuit 12.

In one embodiment, as depicted in FIG. 1C, the power source includes a battery 18 and a pair of capacitors 24 and 26. The battery 18 and a first capacitor 24 are provided outside the capsule 16. A second capacitor 26 is provided inside the capsule 16. The two capacitors 24 and 26 are capacitively coupled together to supply power to the electric circuit 12.

Figure 5:
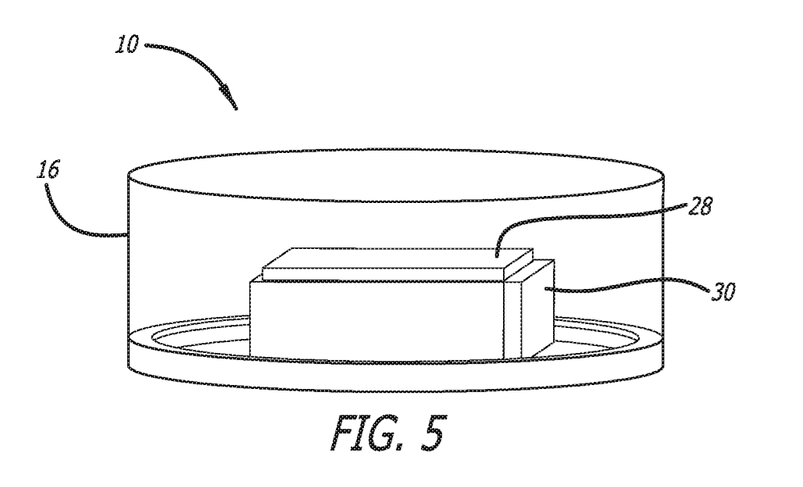
FIG. 5 is a perspective view of a bioabsorbable capsule with an anode and a cathode attached thereto, in accordance with the present invention.

In one embodiment, as depicted in FIG. 5, the power source includes an anode 28 and a cathode 30 provided adjacent the capsule 16.

In one embodiment, the battery 18 is bioabsorbable. In this embodiment, when the bone growth therapy is completed, the capsule 16, the electric circuit 12, and the battery 18, all are consumed by the patient's body, thereby defining a bioabsorbable bone growth stimulator system 10. Exemplary bioabsorbable batteries are shown, for example, in U.S. Pat. No. 8,968,926 and U.S. Pat. No. 8,968,927, which are both hereby incorporated by reference herein in their entirety.

In one embodiment, the battery 18 is biocompatible, but not bioabsorbable, for example, a biocompatible battery used in a cardiac monitoring system, as is well-known in the art. In this embodiment, when the bone growth therapy is completed, the bioabsorbable capsule 16 and the bioabsorbable electric circuit 12 are consumed by the patient's body, but the discharged biocompatible battery 18 remains behind, thereby defining a partially-absorbable bone growth stimulator system 10.

In one embodiment, the battery 18 is a duty cycled, or a pulsed, DC battery, capable of providing a duty cycled, or a pulsed, DC therapy method. As will be understood by persons skilled in the art, a duty cycled, or a pulsed DC therapy method requires less power, and hence less battery capacity, thereby resulting in "energy harvesting" as an alternate power source for the electric circuit 12.

Figure 2:
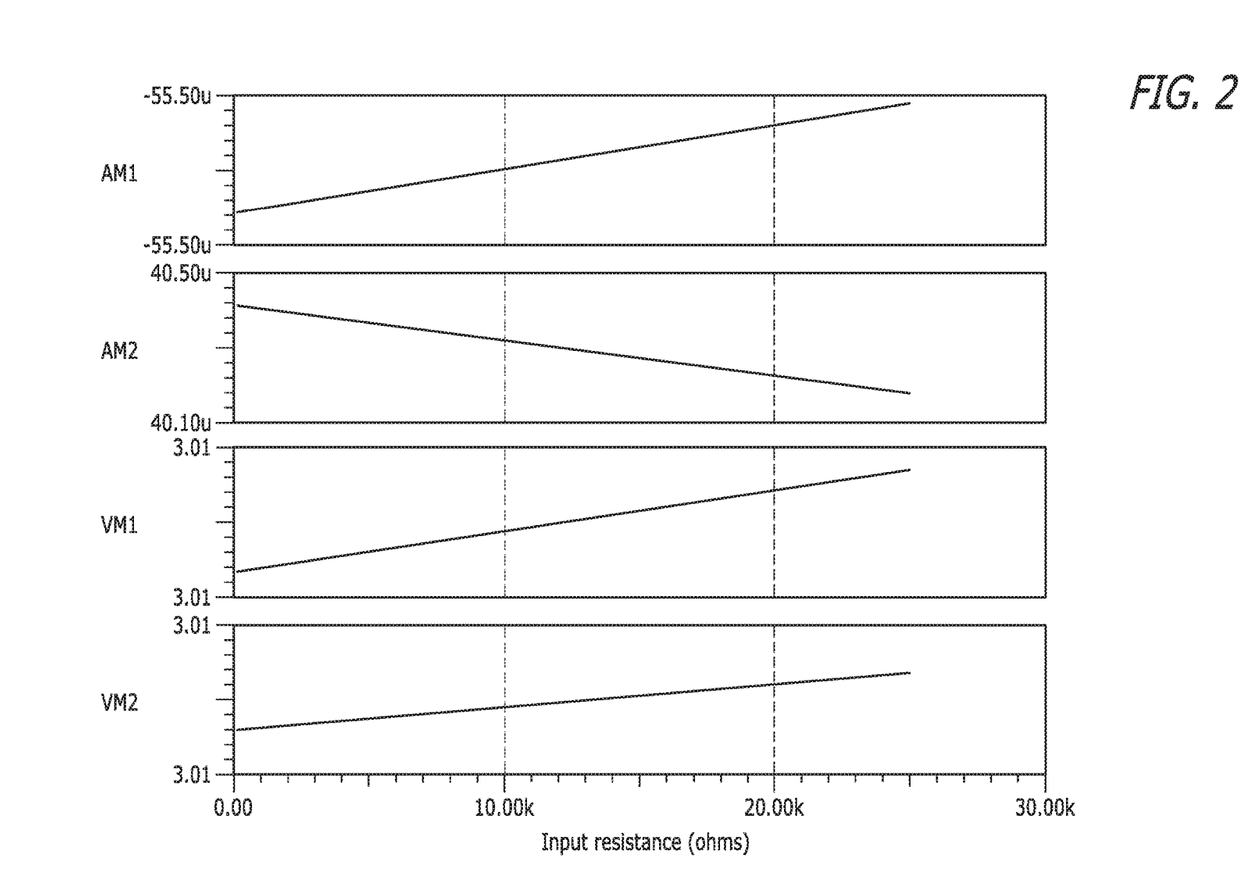
FIG. 2 is a graph depicting constant voltage and current in one embodiment of a bioabsorbable or partially-bioabsorbable bone growth stimulator system in accordance with the present invention.

In one embodiment, as depicted in FIG. 2, the operational amplifier 14 maintains the current and the voltage constant and non-fluctuating in the electric circuit 12.

Figure 4:
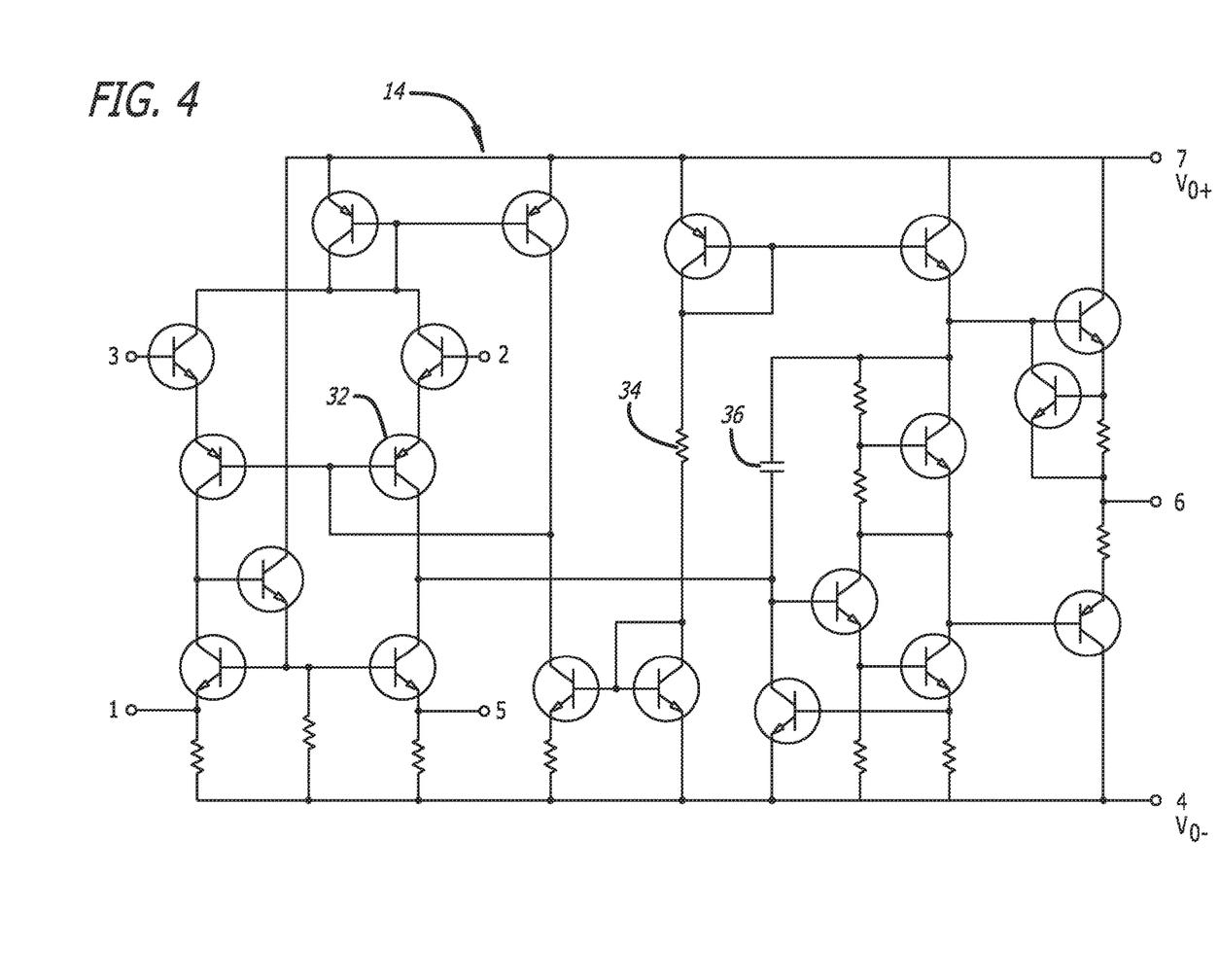
FIG. 4 is a schematic diagram of an operational amplifier configured for use in one embodiment of a bioabsorbable or partially-bioabsorbable bone growth stimulator system in accordance with the present invention.

In one embodiment, as depicted in FIG. 4, the operational amplifier 14 includes twenty transistors 32, ten resistors 34, and one capacitor 36.

The invention, however, is not limited to the above numbers of transistors, resistors, and capacitor(s).

In one embodiment, the electric circuit 12 is manufactured by using a photolithography and polyimide lift-off process. As is known in the art, a layer of polyimide is deposited on top of a substrate. A light-sensitive photo-resist layer is deposited on top of the polyimide layer. A photo-mask, having an outline of the electric circuit defined therein, is provided over the photo-resist layer. Light is shown through the mask, depositing the outline of the electric circuit 12 onto the photo-resist layer. Chemical processes deposit the electrical circuit 12, which is bioabsorbable, and made of one of Mg and MgO onto the substrate. Additional chemical processes remove the photo-resist layer, and lift off the polyimide layer. After the polyimide layer is lifted off, the electric circuit 12 is encapsulated in the water soluble modified alginate capsule 16.

In one embodiment, the battery 18 is provided and electrically coupled to the electric circuit 12, in one of the configurations described above. Voltage applied to the electric circuit 12 by the battery 18 defines the current through the circuit. The operational amplifier 14 maintains constant and non-fluctuating voltage and current in the circuit.

In one embodiment, the bone growth stimulator system 10 is implanted in a patient's body proximate a damaged bone, selected to undergo bone regeneration therapy.

In one embodiment, the bone growth stimulator system 10 is implanted proximate adjacent vertebral bodies, for treatment of various spinal pathologies and disorders, to assist in spinal surgical treatments including, but not limited to, fusion, fixation, correction, partial or complete discectomy, corpectomy, laminectomy, and implantation of spinal implants.

In one embodiment, the flow of current through the electric circuit 12 stimulates regrowth of the spinal bone requiring the therapy.

In one embodiment, the bone growth stimulator system 10 is implanted adjacent an interbody spinal implant, implanted in a disc space between two adjacent vertebral bodies, the implant being at least partially filled with bone growth material. In this embodiment, the flow of current through the electric circuit 12 promotes bone growth through the implant between the adjacent vertebral bodies.

In one embodiment, as discussed above, the selected thickness, and corresponding known dissolution time, of the bioabsorbable capsule 16, results in consumption by the patient's body of at least the bioabsorbable capsule 16 and the electric circuit 12 after completion of the bone regeneration therapy.

In one embodiment, wherein the battery 18 also is bioabsorbable, the power source also is consumed by the patient's body.

Other embodiments of the invention will be apparent to those skilled in the art from consideration of the specification and practice of the invention disclosed herein. It is intended that the specification and the embodiments disclosed in the specification, be considered as exemplary only, with a true scope and spirit of the invention being indicated by the following claims.

We claim:

1. A bone growth stimulator system for use in bone regeneration therapy, the system comprising:
    a bioabsorbable capsule defining an interior cavity, the capsule having a selected capsule thickness, and a known dissolution time;
    bioabsorbable electric circuitry disposed within the interior cavity of the bioabsorble capsule for outputting a bone growth stimulation current, the bioabsorbable electric circuitry including an anode, a cathode, an ammeter, a voltmeter, and an operational amplifier, and at least the ammeter, the voltmeter, and the operational amplifier are made of one of bioabsorbable magnesium and bioabsorbable magnesium oxide; and
    one of a bioabsorbable battery and a biocompatible battery for supplying power to the electric circuitry via an electrical coupling;
    wherein the known dissolution time of the capsule is directly proportional to the selected capsule thickness;
    wherein the selected capsule thickness is selected to bring about dissolution of at least the capsule and the electric circuitry following completion of the bone regeneration therapy; and
    wherein: the voltmeter measures voltage in the electric circuitry adjacent the operational amplifier, the operational amplifier receives a first voltage input corresponding to voltage supplied by the one of the bioabsorbable battery and the biocompatible battery, and receives a second voltage input corresponding to voltage outputted by the operational amplifier, the operational amplifier is configured to maintain current to be constant and non-fluctuating in the electric circuitry, and the bone growth stimulation current is applied via the anode and the cathode.

2. The bone growth stimulator system of claim 1, wherein the battery includes a pulsed DC battery.

3. The bone growth stimulator system of claim 2, wherein the pulsed DC battery provides a DC bone growth therapy delivery method.

4. The bone growth stimulator system of claim 1, wherein the battery is one of directly coupled, inductively coupled, and capacitively coupled, to the electric circuitry.

5. The bone growth stimulator system of claim 1, wherein the battery positioned at one of inside the capsule and outside the capsule.

6. The bone growth stimulator system of claim 1, wherein the system is configured to be implanted proximate at least one vertebral body to stimulate growth of spinal bone tissue.

7. The bone growth stimulator system of claim 1, wherein the capsule is composed of at least water soluble modified alginate.

8. The bone growth stimulator system of claim 1, wherein the ammeter measures amperage from the one of the bioabsorbable battery arid the biocompatible battery.

9. A method of growing bone in a bone regeneration therapy, the method comprising:
    utilizing a bone growth stimulator system, the system comprising:
        a bioabsorbable capsule defining an interior cavity, the capsule having a selected capsule thickness, and a known dissolution time; and
        bioabsorbable electric circuitry disposed within the interior cavity of the bioabsorbable capsule for outputting a bone growth stimulation current, the bioabsorbable electric circuitry including an anode a cathode, an ammeter, a voltmeter, and an operational amplifier and at least the ammeter, the voltmeter, and the operational amplifier are made of one of bioabsorbable magnesium and bioabsorbable magnesium oxide;
        one of a bioabsorbable battery and a biocompatible battery for supplying power to the electric circuitry electrically coupled to the electric circuitry;
    placing the capsule proximate at least one bone;

applying the power to the electric circuitry using the one of the bioabsorbable battery and the biocompatible battery;

measuring, via the voltmeter, voltage in the electric adjacent the operational amplifier;

receiving, at the operational amplifier, a first voltage input corresponding to voltage supplied by e one of the bioabsorbable battery and the biocompatible battery;

receiving, at the operational amplifier, a second voltage input corresponding to voltage outputted by the operational amplifier;

maintaining, at the operational amplifier, current in the electric circuitry constant and non-fluctuating using the operational amplifier;

stimulating bone regeneration in the at least one bone via the output current of the electric circuitry applied via the anode and the cathode; and one of bioabsorbing and partially-bioabsorbing the bone growth stimulator system, wherein the known dissolution time of the capsule is directly proportional to the selected capsule thickness; and wherein the selected capsule thickness is selected to bring about dissolution of at least the capsule and the electric circuitry following completion of the bone regeneration therapy.

10. The method of claim 9, wherein the bioabsorbing the bone growth stimulator system includes bioabsorbing the bioabsorbable capsule, and bioabsorbing the bioabsorbable electric circuitry.

11. The method of claim 9, wherein the partially-bioabsorbing the bone growth stimulator system includes bioabsorbing the bioabsorbable capsule, and bioabsorbing the bioabsorbable electric circuit circuitry.

12. The method of claim 9, further comprises maintaining, with the at least one operational amplifier, the voltage in the electric circuitry substantially constant.

13. The method of claim 9, wherein the applying the power to the electric circuitry includes facilitating application of a pulsed DC voltage to the electric circuitry.

14. The method of claim 13, wherein the application of the pulsed DC voltage defines a pulsed DC therapy delivery method.

15. The method of claim 14, further comprising harvesting energy as an alternative power source.

16. The method of claim 9, wherein the battery is positioned at one of inside the capsule and outside the capsule.

17. The method of claim 16, wherein the battery is one of directly coupled, inductively coupled, and capacitively coupled to the electric circuitry.

18. The method of claim 9, wherein the placing the capsule proximate the at least one bone includes placing the capsule proximate at least one vertebral body.

19. The method of claim 18, wherein the stimulating the bone regeneration in the at least one bone includes stimulating the bone regeneration in the at least one vertebral body.

20. The method of claim 9, wherein the ammeter measures amperage from the one of the bioabsorbable battery and the biocompatible battery.

* * * * *

UNITED STATES PATENT AND TRADEMARK OFFICE
CERTIFICATE OF CORRECTION

Page 1 of 1

PATENT NO. : 10,188,861 B2
APPLICATION NO. : 15/084189
DATED : January 29, 2019
INVENTOR(S) : Stevenson et al.

It is certified that error appears in the above-identified patent and that said Letters Patent is hereby corrected as shown below:

In the Claims

In Column 6, Line 58, in Claim 9, delete "anode" and insert -- anode, --, therefor.

In Column 6, Line 60, in Claim 9, delete "amplifier" and insert -- amplifier, --, therefor.

In Column 7, Line 7, in Claim 9, delete "by e one" and insert -- by the one --, therefor.

In Column 8, Line 4, in Claim 11, delete "electric circuit circuitry." and insert -- electric circuitry. --, therefor.

In Column 8, Line 20, in Claim 17, delete "coupled" and insert -- coupled, --, therefor.

Signed and Sealed this
Twenty-fifth Day of June, 2019

Andrei Iancu
*Director of the United States Patent and Trademark Office*